United States Patent
Prasanna et al.

(10) Patent No.: US 10,055,842 B2
(45) Date of Patent: Aug. 21, 2018

(54) ENTROPY-BASED RADIOGENOMIC DESCRIPTIONS ON MAGNETIC RESONANCE IMAGING (MRI) FOR MOLECULAR CHARACTERIZATION OF BREAST CANCER

(71) Applicant: Case Western Reserve University, Cleveland, OH (US)

(72) Inventors: Prateek Prasanna, Cleveland, OH (US); Nathaniel Braman, Cleveland, OH (US); Anant Madabhushi, Shaker Heights, OH (US); Vinay Varadan, Westlake, OH (US); Lyndsay Harris, Chagrin Falls, OH (US); Salendra Singh, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 55 days.

(21) Appl. No.: 15/397,266

(22) Filed: Jan. 3, 2017

(65) Prior Publication Data
US 2018/0033138 A1 Feb. 1, 2018

Related U.S. Application Data

(60) Provisional application No. 62/368,631, filed on Jul. 29, 2016.

(51) Int. Cl.
*G06K 9/00* (2006.01)
*G06T 7/00* (2017.01)
*G06T 7/11* (2017.01)

(52) U.S. Cl.
CPC ............. *G06T 7/0012* (2013.01); *G06T 7/11* (2017.01); *G06T 2207/10088* (2013.01); *G06T 2207/30068* (2013.01)

(58) Field of Classification Search
CPC ....... G06T 7/0012; G06T 7/0016; G06T 7/11; G06T 7/40; G06T 7/44; G06T 7/45;
(Continued)

(56) References Cited

U.S. PATENT DOCUMENTS

| 6,708,055 | B2 | 3/2004 | Geiser et al. |
| 7,783,092 | B2 | 8/2010 | Agam et al. |
| 9,483,822 | B2 | 11/2016 | Madabhushi et al. |
| 2010/0329529 | A1* | 12/2010 | Feldman .............. G06K 9/6252 382/131 |

(Continued)

OTHER PUBLICATIONS

Notice of Allowance dated Jul. 7, 2016 for U.S. Appl. No. 14/607,145.

*Primary Examiner* — Jose Couso
(74) *Attorney, Agent, or Firm* — Eschweiler & Potashnik, LLC

(57) ABSTRACT

Methods, apparatus, and other embodiments distinguish disease phenotypes and mutational status using co-occurrence of local anisotropic gradient orientations (CoLIAGe) and Laws features. One example apparatus includes a set of circuits that acquires a radiologic image (e.g., MRI image) of a region of tissue demonstrating breast cancer, computes a gradient orientation for a pixel in the MRI image, computes a significant orientation for the pixel based on the gradient orientation, constructs a feature vector that captures a discretized entropy distribution for the image based on the significant orientation, extracts a set of texture features from the MRI image, and classifies the phenotype of the breast cancer based on the feature vector and the set of texture features. Embodiments of example apparatus may generate and display a heatmap of entropy values for the image. Example methods and apparatus may operate substantially in real-time, or may operate in two, three, or more dimensions.

20 Claims, 9 Drawing Sheets

(58) Field of Classification Search
CPC .. G06T 7/62; G06T 7/12; G06T 7/403; G06T 7/404; G06T 7/73; G06T 5/005; G06T 5/20; G06T 2207/10088; G06T 2207/30068; G06T 2207/10081; G06T 2207/20036; G06T 2207/10096; G06T 2207/20021; G06T 2207/20081; G06T 2207/10132; G06T 2207/30016; G06T 2207/30004; G06T 2207/30096; G06T 2207/10116; G06T 2210/41; G06T 2200/04; A61B 5/0013; A61B 5/055; A61B 5/4312; A61B 6/52; A61B 6/502; A61B 6/5211; A61B 6/5217; A61B 8/52; A61B 8/5207; A61B 8/0825; A61B 8/5215; A61B 8/5223; A61B 8/406; G06K 9/00496; G06K 9/00127; G06K 9/00147; G06K 9/00523; G06K 9/34; G06K 9/46; G06K 9/4604; G06K 2017/009; G06K 2209/05; G06F 19/00; G06F 19/30; G06F 19/34; A61K 9/00; A61K 49/06

See application file for complete search history.

(56) References Cited

U.S. PATENT DOCUMENTS

| | | | | |
|---|---|---|---|---|
| 2012/0189176 | A1* | 7/2012 | Giger | G06K 9/6253 382/128 |
| 2012/0249546 | A1* | 10/2012 | Tschirren | G06T 19/00 345/419 |
| 2013/0329973 | A1* | 12/2013 | Cao | A61B 5/0033 382/128 |
| 2015/0087967 | A1* | 3/2015 | Springer, Jr. | G01R 33/56366 600/419 |
| 2015/0227809 | A1* | 8/2015 | Alpert | G06K 9/4671 382/132 |
| 2015/0294063 | A1* | 10/2015 | Kalalakaran | G06F 19/18 702/19 |
| 2015/0332454 | A1* | 11/2015 | Yin | G06T 7/0012 382/131 |
| 2016/0110911 | A1* | 4/2016 | Frank | A61B 5/055 382/131 |
| 2016/0217576 | A1* | 7/2016 | Kabus | A61B 6/469 |
| 2016/0328850 | A1* | 11/2016 | Yin | A61B 5/055 |
| 2017/0046839 | A1* | 2/2017 | Paik | G06K 9/00147 |
| 2017/0148166 | A1* | 5/2017 | Alpert | G06T 7/0012 |

* cited by examiner

ENTROPY-BASED RADIOGENOMIC DESCRIPTIONS ON MAGNETIC RESONANCE IMAGING (MRI) FOR MOLECULAR CHARACTERIZATION OF BREAST CANCER

CROSS REFERENCE TO RELATED APPLICATIONS

This application claims the benefit of U.S. Provisional Application 62/368,361 filed Jul. 29, 2016.

BACKGROUND

Numerous pathologies have different histological phenotypes but similar radiographic appearances. In particular, breast cancer subtypes often have different histological phenotypes but similar radiographic appearances. These similar radiographic appearances may lead to difficulties in differentiating the different subtypes in a clinical environment. For example, the human epidermal growth factor receptor enriched (HER2-E) breast cancer subtype is difficult to distinguish from other subtypes of HER2 positive (HER2+) breast cancer when viewed with magnetic resonance imaging (MRI). HER2+ breast cancer is highly aggressive and insensitive to hormonal therapies. HER2+ breast cancer is also biologically and clinically heterogeneous. PAM50 gene profiling of HER2+ breast cancer identifies the HER2-E subtype as most responsive to HER2-targeted antibody therapy. However, conventional approaches to identifying HER2-E using PAM50 subtyping require expensive and invasive molecular profiling of breast cancer tissue.

Conventional methods for characterizing and distinguishing subtly different pathologies have employed analysis of texture features. However, conventional methods tend to capture global textural patterns. One conventional method that captures global textural patterns employs grey-level co-occurrence matrices (GLCM) and Gabor steerable features to compute global relationships between pixels by averaging responses to various filter operators within a neighborhood to a single global descriptor.

Another conventional approach to distinguishing subtly different pathologies employs local binary patterns (LBP) to provide a pixel-level response that can be used to generate a pixel-level or patch-based classification. Unlike GLCM, LBP provides a signature for every pixel by capturing localized intensity variations across the pixel. However, LBP is highly dependent on the radius parameter, which is critical when extracting local patterns. Additionally, both global and per-pixel texture representations are based on intensity variations and are domain agnostic. However, the histopathological differences between subtly different classes of HER2+ breast cancer may be manifested in differently oriented nuclei, lymphocytes, and glands. These differences in histopathological architecture, which are reflected in MRI imaging, are not reliably captured on a local scale by conventional methods like GLCM or LBP.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
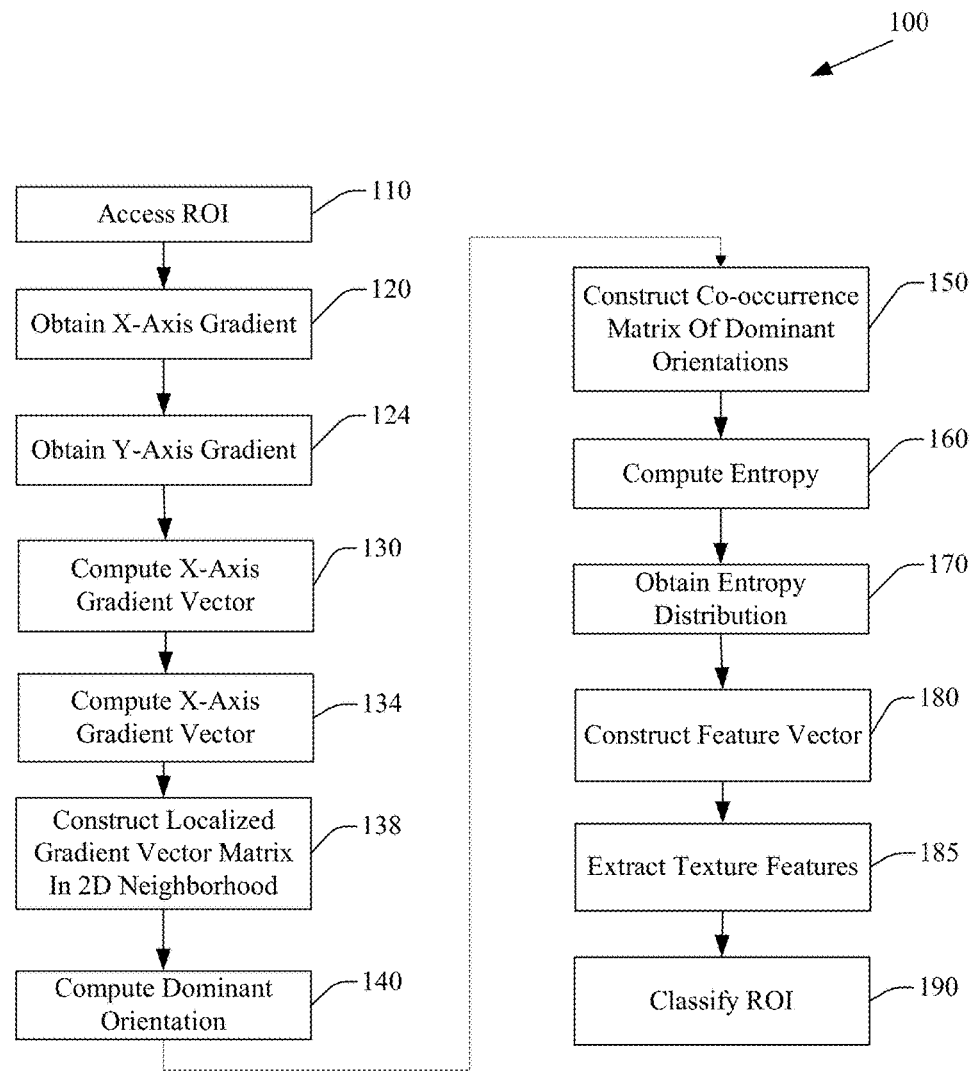
FIG. 1 illustrates an example method of distinguishing molecular phenotypes of breast cancer.

A number of pathologies have different histological phenotypes but similar radiographic appearances. In particular, several molecular sub-types of cancer have different histological phenotypes but similar radiographic appearance. For example, subtypes of HER2+ breast cancer have a similar morphologic appearance when viewed on MRI. However, HER2+ breast cancer subtypes have distinct PAM50 profiles. PAM50 profiling is a molecular test for identifying the genotype of a cancer. PAM50 profiling is, however, invasive and expensive. While conventional systems and methods for classifying cancer phenotypes have employed texture features from radiographic imaging to distinguish subtly different pathologies, conventional texture based approaches capture differences in global intensity patterns. While examples are presented in the context of HER2+ breast cancer, example apparatus and methods may be applied to other similar appearing pathologies for other diseases. Additionally, while examples are presented in the context of MRI, example methods and apparatus may be applied to other types of radiologic imaging, including CT and other types of MRI sequences (e.g. T1, T2, Diffusion, Perfusion).

Example methods and apparatus distinguish different PAM50-identified subtypes of HER2+ breast cancer by employing co-occurrence of local anisotropic gradient orientations (CoLIAGe) to capture higher order occurrence patterns of local gradient tensors expressed at a pixel level of a dynamic contrast enhanced (DCE) MRI image, and by using Laws energy measures to detect textural patterns expressed in the DCE-MRI image that are associated with incoherent vasculature or inhomogeneous structures. Example methods and apparatus capture neighborhood orientation variation with a localized gradient tensor field. The localized gradient tensor field reflects the underlying cellular arrangement of a phenotype being imaged. Example methods and apparatus compute a co-occurrence matrix on the localized gradient tensors. The co-occurrence matrix captures co-occurring patterns of orientation disorder locally.

Example methods and apparatus also extract a set of texture features, including Laws energy measures, from a DCE-MRI image of a region of tissue demonstrating breast cancer. Laws energy measures indicate textural patterns that differentiate HER2-E from non-HER2-E breast cancers. HER2-E cancer tissue is characterized by a high expression of speckle-detecting Laws features near cancer borders. The speckled contrast enhancement may be caused by incoherent vasculature associated with HER2-E tissue in the cancer. HER2-E cancer tissue is also characterized by inhomogeneous enhancement or structure at the cancer focus. Example methods and apparatus extract Laws features that detect enhancement ripple-like patterns of HER2-E tissue. A rippled region is a region of hyper intensity surrounded by fluctuating enhancement. HER2-E tissue is characterized by a high expression of ripple-detecting features near the cancer focus. Example methods and apparatus may extract other Laws texture features that distinguish between HER2-E and non-HER2-E tissue, including wave features, spottiness features, or edge features.

Example methods and apparatus associate computer-extracted imaging features with disease specific genomic information, including mutational status. Example methods and apparatus employ kinetic analysis of textural changes within breast cancer lesions on DCE-MRI images to more accurately distinguish between HER2-E and non-HER2-E breast cancer, and between TP53 mutational statuses, than conventional methods. Example methods and apparatus quantitatively measure the degree of order and disorder (e.g., entropy) of localized image gradient orientations. Example methods and apparatus capture the entropy features derived from the co-occurrence of pixel level gradient orientations in DCE-MRI images. Example methods and apparatus are independent of the absolute signal intensities found in DCE-MRI images and are therefore more robust to DCE-MRI drift across scanners than conventional methods. Example methods and apparatus enable quantification of subtle micro-textural changes that may not be captured by conventional methods, including Response Evaluation Criteria in Solid Tumors (RECIST), MRI signal intensity, or pharmacokinetic (PK) parameters. Embodiments of example methods and apparatus capture DCE-MRI images using 1.5 T or 3.0 T magnets, STIR axial and T1 weighted fat saturation axial images, and 8 or 16 channel dedicated breast coils. Other embodiments may employ different magnets, image types, or coils.

In one embodiment, a dataset of forty-two HER2+ DCE-MRI breast cancer cases with subtypes identified using the PAM50 gene expression signature is acquired. Hierarchical clustering using PAM50 genes is used to identify sub-groups corresponding to ER/PR immunohistochemistry, as well as luminal cluster and proliferation genes. In this embodiment, the distribution of subtypes includes 19 HER2-E, 18 HER2-luminal (HER2-L) and 5 HER2-basal (HER2-B) cases. In this embodiment, before and after intravenous Gd-contrast administration images are acquired using a 1.5/3.0 T magnet, STIR axial and T1w fat saturation axial scans with an 8 or 16 channel dedicated breast coil. Cancer regions are delineated on the peak enhancement phase followed by pixel-wise computation of gradient orientations on the annotated ROI. Local dominant orientations are computed via principal component analysis (PCA) and entropy features are extracted on a per-pixel basis from the co-occurrence matrix of the dominant orientations.

In this embodiment, first order entropy statistics are used to identify groups (e.g., HER2-E, HER2-L, HER2-B) in a hierarchical unsupervised cluster setting. Mean CoLIAGe entropy distinguishes HER2-E from HER2-basal+luminal while kurtosis and skewness of CoLIAGe features distinguishes HER2-B from HER2-enriched+luminal. Using at least five entropy statistics, including kurtosis, skewness, mean, median, or standard deviation, example methods and apparatus may identify three distinct clusters in an unsupervised fashion. These three distinct clusters correspond to three different subtypes as identified by a PAM50 assay of the dataset, with HER2-enriched+basal identified with a clustering accuracy of at least 70%. Conventional approaches using PK parameters and signal intensity result in a corresponding clustering accuracy of only 54%. Thus, example methods and apparatus employing CoLIAGe improve on conventional approaches to breast cancer imaging because on baseline imaging (e.g., pre-biopsy), example methods and apparatus stratify HER2+ cases into distinct subtypes based on cellular lineage hormone receptor status, and by facilitating greater understanding of the associated biological heterogeneity within the cancer microenvironment across subtly different subtypes. Radiologic phenotypes are a reflection of cellular/molecular phenotypes. While conventional approaches quantify intra-tumoral permeability changes, example methods and apparatus capture the degree of order in pixel-level gradient orientations within local neighborhoods of the cancer habitat, thus facilitating quantification of subtle micro-textural changes and cancer heterogeneity that may not be captured by conventional approaches.

Methods and apparatus described herein may also distinguish the TP53 mutational status of breast cancer tissue represented in a DCE-MRI image. In one embodiment, example methods and apparatus distinguish TP53 mutational status using directional gradient based radiogenomic descriptors captured by CoLIAGe. TP53 mutation is associated with poor patient response to therapy. Example methods and apparatus predict preoperative treatment response based on TP53 mutation. TP53 inactivation creates disorder across multiple spatial scales. Uncontrolled cytoskeleton formation distorts micro-architecture, while unregulated division creates disordered cell clusters. Example methods and apparatus employ second order statistical features derived from CoLIAGe to predict TP53 mutational status.

In one embodiment, breast cancer tissue samples are obtained from a set of patients and whole-exome DNA sequencing is performed with an average coverage of 100×. In this embodiment, twenty-four breast cancer tissue samples from the set are annotated as harboring non-synonymous TP53 mutations as TP53$^{MUT}$. Another twenty samples from the set are classified as TP53$^{WT}$. In this embodiment, 1.5 T or 3.0 T short TI inversion recovery (STIR) and T1w fat saturation axial MRI scans are obtained with an 8 or 16 channel dedicated breast coil. Patients may be imaged after administration of a gadolinium (Gd) contrast agent through intravenous injection, and breast cancer extent is annotated onto images by a radiologist, or may be annotated automatically. Example methods and apparatus may employ supervised hierarchical clustering of CoLIAGe parameters to identify features that distinguish TP53$^{MUT}$ and TP53$^{WT}$.

In this embodiment, skewness and kurtosis of the information measure of correlation are employed as discriminating radiogenomic features. Example methods and apparatus may employ the skewness and kurtosis of the information measure of correlation to achieve an accuracy of 74% in distinguishing $TP53^{MUT}$ from $TP53^{WT}$. Example methods and apparatus may employ additional distinguishing features including the skewness of CoLIAGe inertia, sum average, or difference variance, and may also employ the kurtosis of other orientation co-occurrence statistics, including energy, entropy, or correlation, to use in an eight feature unsupervised clustering, which identifies $TP53^{MUT}$ with an accuracy of 100% and $TP53^{WT}$ with an accuracy of 65%. $TP53^{WT}$ over-expresses skewness and kurtosis of the information measure of correlation while these features are under-expressed in $TP53^{MUT}$.

Example methods and apparatus thus improve on conventional methods by capturing an orientation variation across neighboring pixels characteristic to a particular pathology through the aggregation of cellular activity and structure in a localized region. For example, methods and apparatus described herein distinguish HER2-E from non-HER2-E tissue with an average area under the curve (AUC) accuracy of at least 0.72, +/−0.06, compared with conventional PK parameter approaches that achieve an average AUC of only 0.50, +/−0.09 (i.e. no better than random guessing). By increasing the accuracy with which mutational status or subtly different pathologies of cancer are distinguished, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a computerized method 100 for distinguishing disease phenotypes using CoLIAGe and Laws features. Method 100 includes, at 110, accessing a region of interest (ROI) in a volume illustrated in a dynamic contrast enhanced (DCE) magnetic resonance image (MRI). The ROI may be a two dimensional ROI. As described below, the ROI may be a three dimensional ROI. The ROI has a set of pixels. A pixel in the set of pixels has an intensity. In one embodiment, the ROI is defined as $\mathcal{C}=(C,f)$. f(c) is an associated intensity at a first pixel c on a three dimensional (3D) grid C. In one embodiment, the DCE-MRI is of a section of breast cancer tissue. Accessing an ROI includes acquiring electronic data, reading from a computer file, receiving a computer file, reading from a computer memory, or other computerized activity. In one embodiment, the volume illustrated in the ROI is associated with a DCE-MRI image of a patient demonstrating pathology associated with breast cancer. In other embodiments, different types of cancerous tissue may be imaged using different imaging techniques.

Method 100 also includes, at 120, obtaining an x-axis gradient for a first pixel in the set of pixels. The x-axis gradient is based, at least in part, on the intensity of the pixel. Method 100 also includes, at 124, obtaining a y-axis gradient for the first pixel. The y-axis gradient is based, at least in part, on the intensity of the pixel. In one embodiment, obtaining the x-axis gradient for the first pixel and obtaining the y-axis gradient for the first pixel includes computing $$\nabla f(c) = \frac{\partial f(c)}{\partial X}\hat{\imath} + \frac{\partial f(c)}{\partial Y}\hat{\jmath}.$$

In this embodiment, $$\frac{\partial f(c)}{\partial X}$$

represents the gradient magnitude along the x-axis, and $$\frac{\partial f(c)}{\partial Y}$$

represents the gradient magnitude along the y-axis.

Method 100 also includes, at 130, computing an x-axis gradient vector for a second pixel. The second pixel is in an N pixel by N pixel neighborhood centered around the first pixel. N is a number. N may be adjustable by a user. Method 100 also includes, at 134, computing a y-axis gradient vector for the second pixel in the N pixel by N pixel neighborhood. In one embodiment, computing the x-axis gradient vector for the second pixel in the N pixel by N pixel neighborhood centered around the first pixel includes computing $\vec{\partial f}_X(c_k)$, where $k \in \{1, 2, \ldots, N^2\}$. Computing the y-axis gradient vector for the second pixel includes computing $\vec{\partial f}_Y(c_k)$, where $k \in \{1, 2, \ldots, N^2\}$.

Method 100 also includes, at 138, constructing a localized gradient vector matrix. The localized gradient vector matrix is based, at least in part, on the x-axis gradient vector for the second pixel, and the y-axis gradient vector for the second pixel. In one embodiment, the localized gradient vector matrix is defined as $\vec{F}=[\vec{\partial f_X}(c_k)\, \vec{\partial f_Y}(c_k)]$. In one embodiment, the gradient vector matrix may be constructed for a two dimensional neighborhood having dimensions $N^2 \times 2$.

Method 100 also includes, at 140, computing a dominant orientation for the first pixel. The dominant orientation is based, at least in part, on the localized gradient vector matrix. In one embodiment, computing the dominant orientation for the first pixel includes calculating $$\phi(c) = \tan^{-1}\frac{r_Y^k}{r_X^k},$$

where $r_X^k$ represents the dominant principal component in X, and where $r_Y^k$ represents the dominant principal component in Y. In this embodiment, $k \in \{1, 2, \ldots, N^2\}$. $r_X^k$ and $r_Y^k$ are obtained using principal component analysis (PCA). In one embodiment, the dominant orientation may be computed using principal component analysis (PCA). In another embodiment, the dominant orientation may be computed using other, different types of analysis.

Method 100 also includes, at 150, constructing a co-occurrence matrix of dominant orientations from the dominant orientation. In one embodiment, the co-occurrence matrix is an N×N matrix $\mathcal{M}$. The co-occurrence matrix $\mathcal{M}$ captures orientation pairs between pixels that co-occur in a neighborhood $W_1$. In this embodiment, $$M_{w_i}(p, q) = \sum_{c_j, c_k}^{w_i} \sum_{p,q=1}^{N} \begin{cases} 1, & \text{if } \phi(c_j) = p \text{ and } \phi(c_k) = q \\ 0, & \text{otherwise} \end{cases}.$$

A discretized dominant orientation for a pixel $c_k$ is represented by $\bar{\phi}(c_k)$.

$$\bar{\phi}(c_k) = \omega \times \text{ceil}\left(\frac{\phi(c_k)}{\omega}\right),$$

where $\omega$ is a discretizing factor.

$$N = \frac{180}{\omega}$$

represents a number of discrete angular bins. $\omega$ may be adjusted to alter the number of discrete angular bins. In another embodiment, the floor function may be used instead of the ceiling function.

Method 100 also includes, at 160 computing an entropy for the first pixel. The entropy is based, at least in part, on the co-occurrence matrix. In one embodiment, computing the entropy $\varepsilon$ for the first pixel includes computing $\varepsilon(c) = \Sigma_{p,q} - \mathcal{M}(p,q)\log(\mathcal{M}(p,q))$.

Method 100 also includes, at 170, obtaining a distribution of the entropy. In one embodiment, obtaining the distribution for the entropy includes computing a histogram of $\varepsilon$. The histogram of E is computed by aggregating $\varepsilon(c_k)$, $k \in \{1, \ldots, |C|\}$, where $|C|$ is the cardinality of C. The histogram is divided into a plurality of bins. A bin has a size $\nu$. Bin size may be optimized based on a training set associated with the disease phenotypes being distinguished.

Method 100 also includes, at 180, constructing a feature vector. The feature vector is based, at least in part, on the distribution of the entropy. In one embodiment, the feature vector is a $\nu \times 1$ vector F. The values for the bin size $\nu$ and neighborhood dimension N may be obtained by employing a support vector machine classifier using a 3-fold cross-validation strategy to obtain optimum values for $\nu$ and N. In one embodiment, $\nu=30$ and $N=7$. In another embodiment, other values for $\nu$ and N may be employed.

Method 100 also includes, at 185, extracting a set of texture features from the ROI. The set of texture features includes Laws features. A Laws feature may be obtained by processing the image with filters that detect a combination of spatial intensity patterns, such as speckling, rippling, waves, spottiness, or edges. Laws features capture a combination of texture patterns: one in the x direction and one in the y direction. Laws filters are created by combining two one-dimensional (1D) filters that capture one of five texture patterns, including speckling, spottiness, rippling, waves or edges. The two 1D filters may thus be combined in twenty-five different ways, leading to twenty-five different Laws features. Thus, the set of texture features may include a Laws feature computed based on a two dimensional (2D) filter targeting speckling, rippling, waves, spots, or edges represented in the volume illustrated in the MRI. In one embodiment, a subset of discriminative texture features may be selected from the set of texture features using a minimum redundancy maximum relevance (mRMR) approach, based, at least in part, on the correlation between a member of the set of texture features and the HER2-E status of the region of tissue represented in the image. In another embodiment, other dimensionality-reduction/feature selection techniques, including unsupervised clustering, Wilcoxon Rank sum test or local embedding approaches, may be employed to select discriminative texture features from the ROI.

Method 100 also includes, at 190, controlling a phenotype classifier to classify the ROI based, at least in part, on the feature vector and the set of texture features. In one embodiment, controlling the phenotype classifier to classify the ROI includes identifying phenotypic imaging signatures of a plurality of molecular sub-types of breast cancer. The plurality of sub-types includes HER2-E and non-HER2-E tissue. In one embodiment, a computer aided diagnostic system (CADx) is controlled by method 100 to distinguish the disease phenotype found in the ROI. The CADx calculated distinction may then be employed to complement a human pathologist's determination that the ROI represents a first disease phenotype or a second, different phenotype. In another embodiment, the phenotype classifier may distinguish phenotypes of other types of cancer, including prostate cancer and lung cancer.

In one embodiment controlling the phenotype classifier to classify the ROI includes distinguishing HER2-E breast cancer subtype from HER2+ breast cancer in the ROI. Controlling the phenotype classifier may also include distinguishing HER2-E from HER2-L breast cancer or HER2-B breast cancer. Controlling the phenotype classifier may also include distinguishing HER2-B from HER2-E or HER2-L. Method 100 controls the phenotype classifier to distinguish HER2-E from HER2-L or HER2-B based, at least in part, on a mean entropy. In one embodiment, the phenotype classifier distinguishes HER2-E from HER2-L or HER2-B based, at least in part, on the feature vector, the entropy, the distribution of the entropy, or based on statistics computed from the feature vector, the entropy, or the distribution of the entropy. Method 100 may also control the phenotype classifier to distinguish HER2-B from HER2-E or HER2-L based, at least in part, on a kurtosis value and a skewness value.

Figure 2:
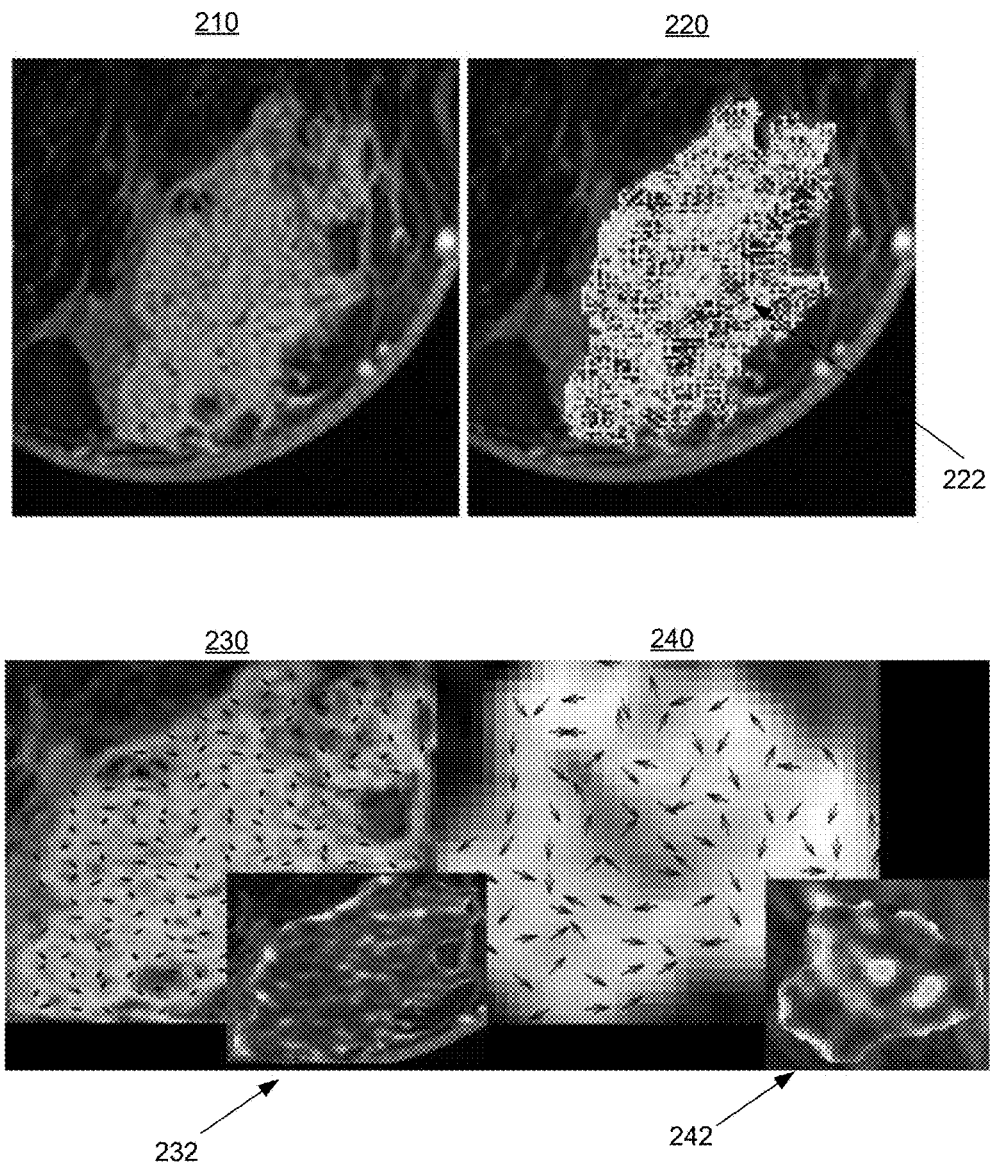
FIG. 2 illustrates Laws features and co-occurrence of local anisotropic gradient orientations (CoLlAGe) features in MRI images of breast cancer tissue.

FIG. 2 illustrates Laws features and CoLIAGe features represented in MRI images of breast cancer tissue. Image 210 is an ROI of a volume illustrated in a DCE-MRI image of a region of tissue demonstrating HER2-E. Image 220 illustrates the same ROI with Laws features that capture speckled contrast enhancement patterns 222. The speckled contrast enhancement patterns 222 highlight sub-visual patterns that indicate an erratic vasculature. Image 230 illustrates a region of tissue demonstrating HER2-E breast cancer subtype. The gradient disorder of image 230 is expressed by a first heatmap 232. Image 240 illustrates a region of tissue demonstrating non-HER2-E breast cancer. A second heatmap 242 expresses the relatively lower level of gradient disorder demonstrated by the non-HER2-E region. First heatmap 232 of HER2-E tissue demonstrates significantly higher variance than second heatmap 242 which corresponds to non-HER2-E tissue.

Figure 6:
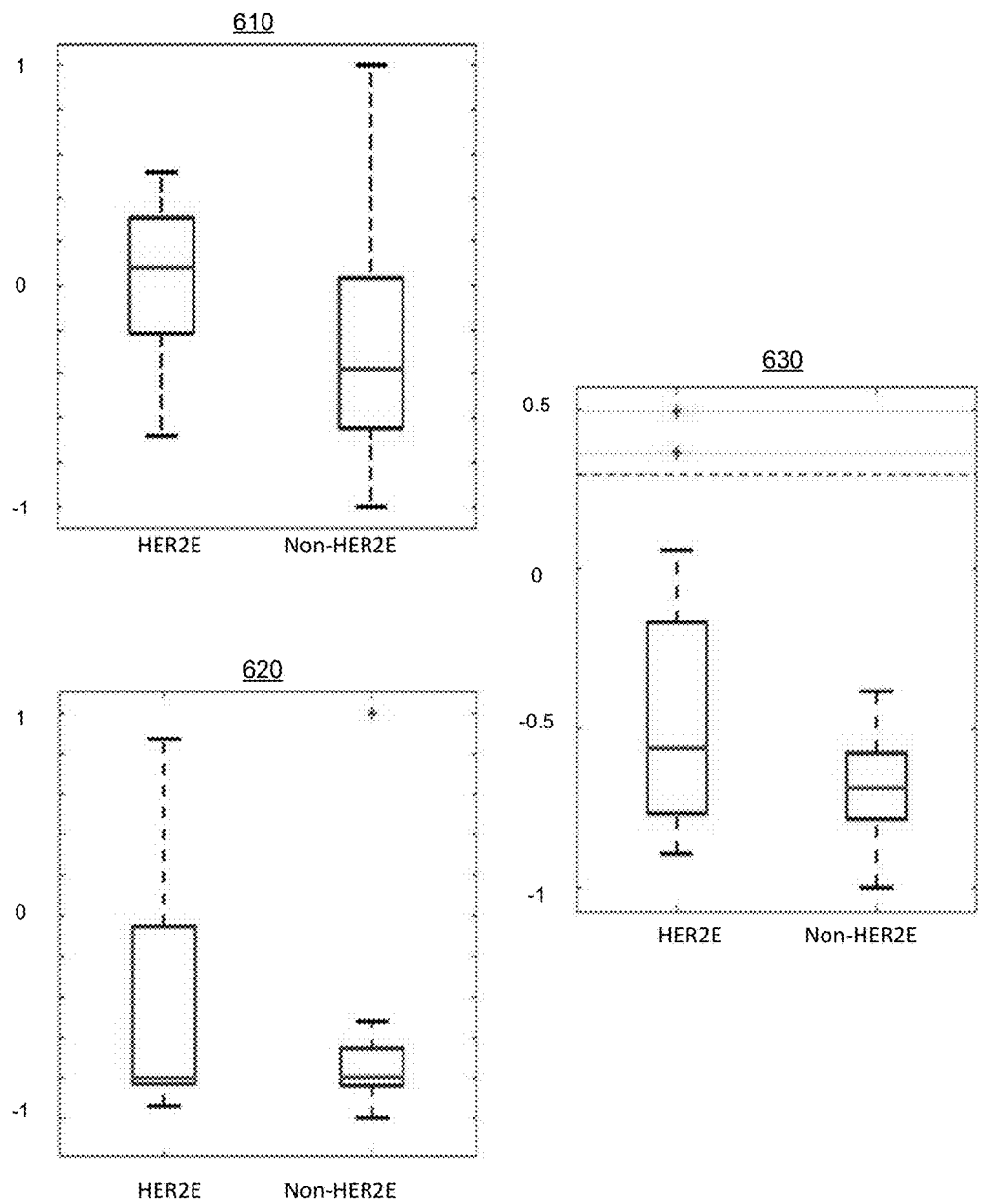
FIG. 6 illustrates box plots of features associated with HER2-E and non-HER2-E tissue.

FIG. 6 illustrates box plots of Laws and CoLIAGe features associated with HER2-E and non-HER2-E tissue. Box plot 610 illustrates the distribution of Laws speckle features between HER2-E and non-HER2-E tissue. Box plot 620 illustrates the distribution of Laws ripple-speckle features between HER2-E and non-HER2-E tissue. Box plot 610 illustrates higher speckling in HER2-E tissue compared to non-HER2-E tissue. Box plot 620 illustrates higher variance of ripple-speckle features in HER2-E tissue compared to non-HER2-E tissue. Box plot 630 plots kurtosis of entropy distribution between HER2-E and non-HER2-E tissue. As illustrated in box plot 630, HER2-E has a higher variance than non-HER2-E.

TP53 mutation is associated with poor patient response to therapy. TP53 is a marker of breast cancer prognosis. TP53 inactivation creates disorder across multiple spatial scales. Uncontrolled cytoskeleton formation distorts micro-architecture, while unregulated division creates disordered cell clusters. Example methods and apparatus predict preoperative treatment response based on TP53 mutation. Example methods and apparatus employ CoLIAGe to predict TP53 mutational status. Thus, better identification of TP53 mutational status achieved by method 100 may improve patient outcomes by more effectively modulating breast cancer treatments.

In one embodiment, controlling the phenotype classifier to classify the ROI includes predicting a TP53 mutational status of breast cancer tissue represented in the ROI. Predicting a TP53 mutational status comprises computing a skewness measure of correlation and a kurtosis measure of correlation based on the co-occurrence matrix. Predicting a TP53 mutational status further comprises classifying the ROI as $TP53^{MUT}$ or $TP53^{WT}$ based, at least in part, on the feature vector, the skewness measure, and the kurtosis measure. The skewness measure may include an inertia feature, a sum average feature, or a difference feature variance. The kurtosis measure may include an energy feature, an entropy feature, or a correlation feature.

Figure 7:
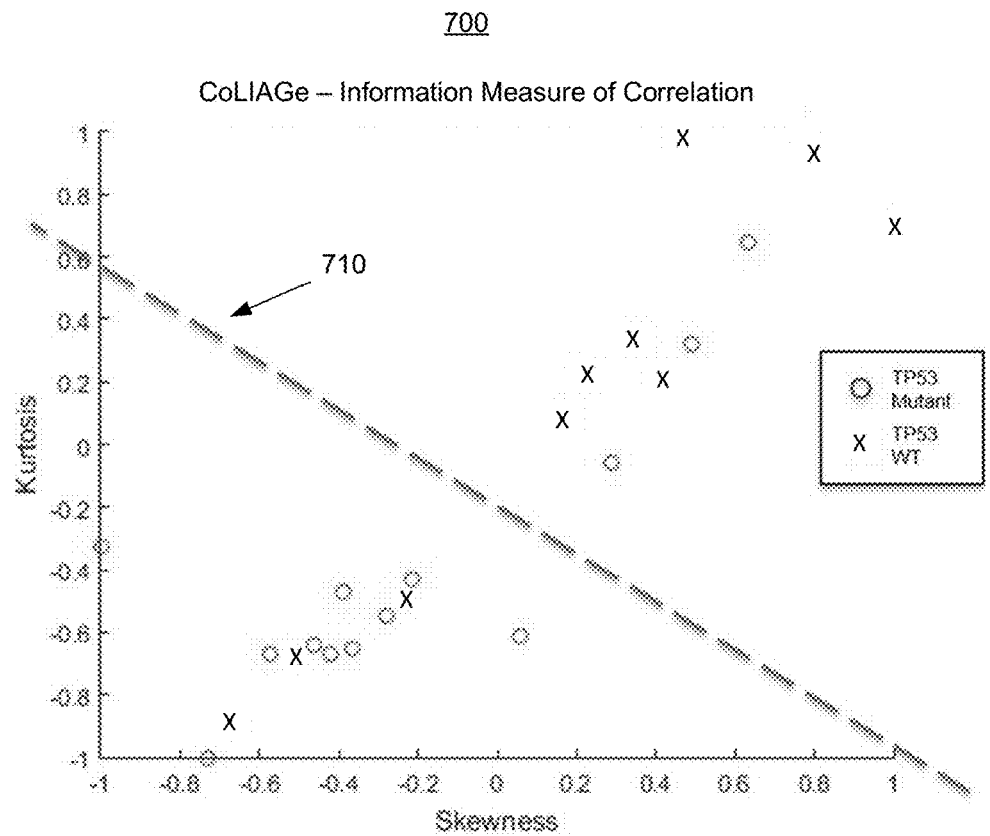
FIG. 7 is a graph of skewness vs. kurtosis of the information measure of correlation for different TP53 mutational statuses.

FIG. 7 illustrates a graph 700 representing skewness vs. kurtosis of the information measure of correlation for a study of TP53 images. Kurtosis and skewness of the CoLIAGe information measure of correlation distinguish $TP53^{MUT}$ images, represented by circles on the graph 700, from $TP53^{WT}$, represented by x's on the graph 700. Recall that kurtosis and skewness may be computed from the CoLIAGe feature value obtained from a voxel in an MRI image. Example methods and apparatus facilitate distinguishing TP53 mutational status with an accuracy of at least 74%, as indicated by the dashed line 710.

Figure 8:
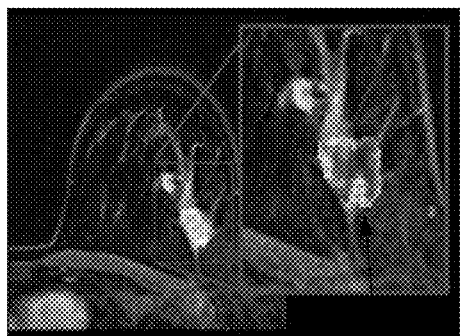
FIG. 8 illustrates differences of expression of the information measure of correlation for different TP53 mutational statuses.
Figure 8:
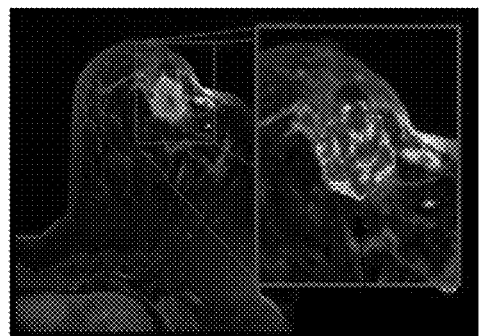

FIG. 8 illustrates differences of expression of the information measure of correlation for a $TP53^{WT}$ image 810 and a $TP53^{MUT}$ image 820. CoLIAGe map 812 is overlaid on $TP53^{WT}$ image 810, illustrating a qualitative heatmap of CoLIAGe values associated with $TP53^{WT}$ mutational status. CoLIAGe map 822 is overlaid on $TP53^{MUT}$ image 820, illustrating a qualitative heatmap of CoLIAGe values associated with $TP53^{MUT}$ mutational status.

Improved distinction of disease phenotypes or mutational status using CoLIAGe and Laws features may produce the technical effect of improving treatment efficacy by increasing the accuracy of and decreasing the time required to differentiate disease phenotypes in a patient. Treatments and resources may be more accurately tailored to patients with a particular subtype of cancer so that more appropriate treatment protocols may be employed.

Using a more appropriately modulated treatment may lead to less aggressive therapeutics being required for a patient or may lead to avoiding or delaying a biopsy, a resection, or other invasive procedure. When disease phenotypes or mutational statuses are more quickly and more accurately distinguished, patients most at risk may receive a higher proportion of scarce resources (e.g., therapeutics, physician time and attention, hospital beds) while those less at risk may be spared unnecessary treatment, which in turn spares unnecessary expenditures and resource consumption. Example methods and apparatus may thus have the effect of improving patient outcomes.

While FIG. 1 illustrates processing x-axis gradients and y-axis gradients for a two dimensional ROI, example methods are not so limited. For example, a method may also process z-axis gradients and operate on a 3D ROI. When operating on x, y, and z-axis gradients for a 3D ROI, methods may include obtaining a z-axis gradient, defining a neighborhood voxel size (e.g., N×N×N) and constructing the localized gradient vector matrix with a dimension of $N^3 \times 3$.

While FIG. 1 illustrates various actions occurring in serial, it is to be appreciated that various actions illustrated in FIG. 1 could occur substantially in parallel. By way of illustration, a first process could involve capturing x-axis and y-axis gradients in an ROI, a second process could involve constructing a localized gradient vector matrix, and a third process could involve extracting texture features, including Laws features, from the ROI. While three processes are described, it is to be appreciated that a greater or lesser number of processes could be employed and that lightweight processes, regular processes, threads, and other approaches could be employed.

Figure 3:
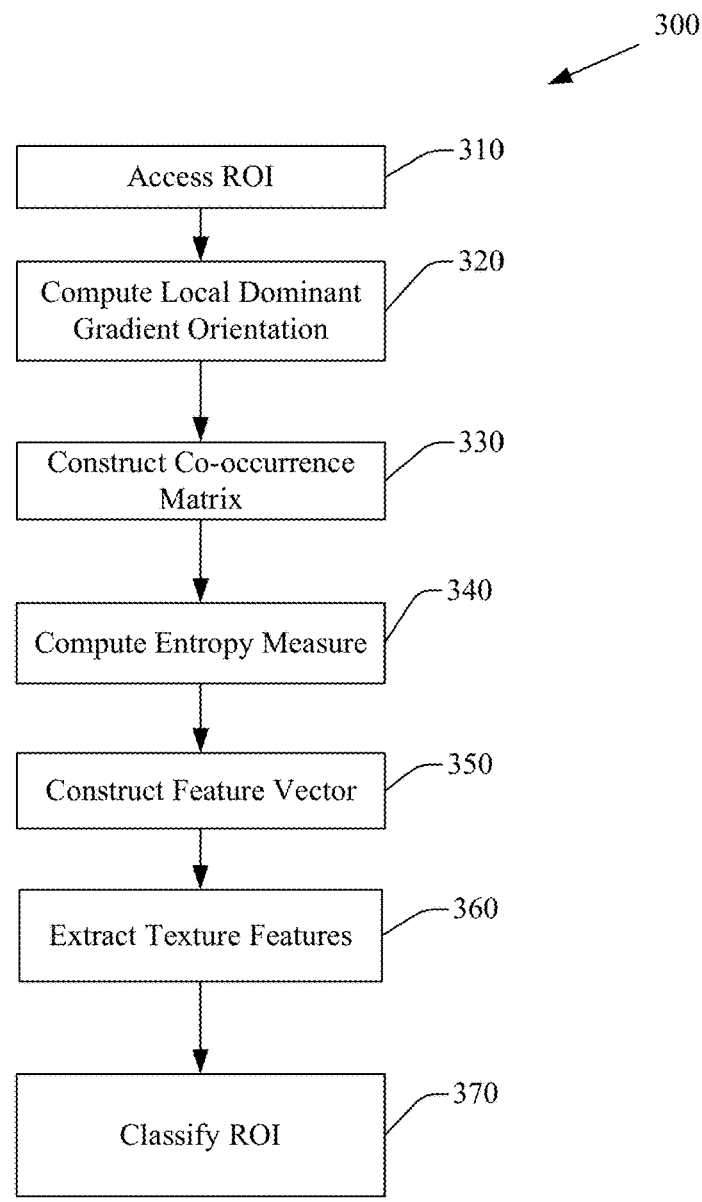
FIG. 3 illustrates an example method of distinguishing molecular phenotypes of breast cancer.

FIG. 3 illustrates an example method 300 for distinguishing disease phenotypes or mutational status. Method 300 includes, at 310, accessing an ROI in a volume illustrated in a DCE-MRI image. The ROI includes a set of pixels. A pixel in the set of pixels has an intensity.

Method 300 also includes, at 320, computing a local dominant gradient orientation for a first pixel in the set of pixels. In one embodiment, computing the local dominant gradient orientation for the first pixel includes obtaining a set of gradients for the first pixel along a plurality of axes. Computing the local dominant gradient orientation for the first pixel also includes computing a gradient orientation for the pixel based, at least in part, on the set of gradients. Computing the local dominant gradient orientation also includes computing a set of gradient vectors for a plurality of pixels in a local neighborhood. In one embodiment, the local neighborhood is centered on the first pixel, and the neighborhood dimensions are user-definable. Computing the local dominant gradient orientation also includes constructing a localized gradient vector matrix from the set of gradient vectors. Computing the local dominant gradient orientation also includes computing the local dominant gradient orientation for the first pixel using PCA. The PCA is based on the localized gradient vector matrix. In another embodiment, the local dominant gradient may be computed using other, different approaches.

Method 300 also includes, at 330, constructing a co-occurrence matrix for the set of pixels, based, at least in part, on the local dominant orientation. In one embodiment, constructing the co-occurrence matrix includes discretizing the local dominant gradient orientation for the first pixel. Constructing the co-occurrence matrix also includes populating the co-occurrence matrix with local dominant gradient orientation pairs that co-exist between pixels in the neighborhood.

Method 300 also includes, at 340, computing an entropy measure for the set of pixels based, at least in part, on the co-occurrence matrix. In one embodiment, computing the entropy measure includes aggregating the entropy measures for elements of a subset of the set of pixels. The entropy measure is based, at least in part, on the co-occurrence matrix. Computing the entropy measure also includes constructing a histogram of the entropy measure for the set of pixels. The histogram is divided into bins. The bins are discrete bins. A bin may have a threshold size. The threshold size may be adjustable by a user to accommodate different disease phenotypes or mutational statuses. For example, a first disease phenotype may be distinguished from a second disease phenotype using a first bin size, while a third disease phenotype may be distinguished from the first disease phenotype more accurately using a second, different bin size. Similarly, a first mutational status may be distinguished from a second mutational status using a first bin size.

Method 300 also includes, at 350, constructing a feature vector based on a distribution of the entropy measure. Constructing the feature vector includes extracting entropy measure values from a distribution of the histogram.

Method 300 also includes, at 360, extracting a set of texture features from the ROI. The set of texture features may include Laws energy measures. The set of texture features may include a speckling feature, a ripple feature, a wave feature, a spottiness feature, or an edge feature. In another embodiment, other texture features may be extracted.

Method 300 also includes, at 370, controlling a disease phenotype classification system to classify the ROI based, at least in part, on the feature vector and the set of texture features. In one embodiment, controlling the disease phenotype classification system to classify the ROI includes classifying the ROI as HER2-E, HER2-L, or HER2-B. In another embodiment, controlling the disease phenotype classification system to classify the ROI includes predicting a mutational status of the ROI as $TP53^{MUT}$ or $TP53^{WT}$. In one embodiment, controlling the disease phenotype classification system includes constructing a heatmap based on the feature vector. In this example, hot areas of the heatmap represent high entropy values and cool areas of the heatmap represent low entropy values. Classifying the ROI using the heatmap based on the feature vector or the set of texture features provides improved accuracy compared to conventional methods of distinguishing disease phenotypes that employ GLCM, HoG, Haralick, or LBP. In another embodiment, statistical displays other than heatmaps may be employed to represent entropic values across the ROI, and different color schemes may be employed to represent areas of low entropy and areas of high entropy.

Example methods and apparatus leverage pixel-level gradient orientation entropy and Laws energy measures that capture cellular disorder that is not analyzed by conventional methods. Example methods and apparatus facilitate making more accurate distinctions of disease phenotypes or mutational statuses. Improving disease phenotype or mutational status distinction improves the allocation of resources, personnel, and therapeutics to appropriate patients while sparing other patients from treatment that might have been prescribed with a less accurate distinction. For example, breast cancer phenotypes or mutational statuses that are difficult to distinguish using conventional MRI methods may be distinguished by example methods and apparatus faster, more accurately, and without the need for surgical biopsy.

In one example, a method may be implemented as computer executable instructions. Thus, in one example, a computer-readable storage medium may store computer executable instructions that if executed by a machine (e.g., computer) cause the machine to perform methods described or claimed herein including method 100 and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 4:
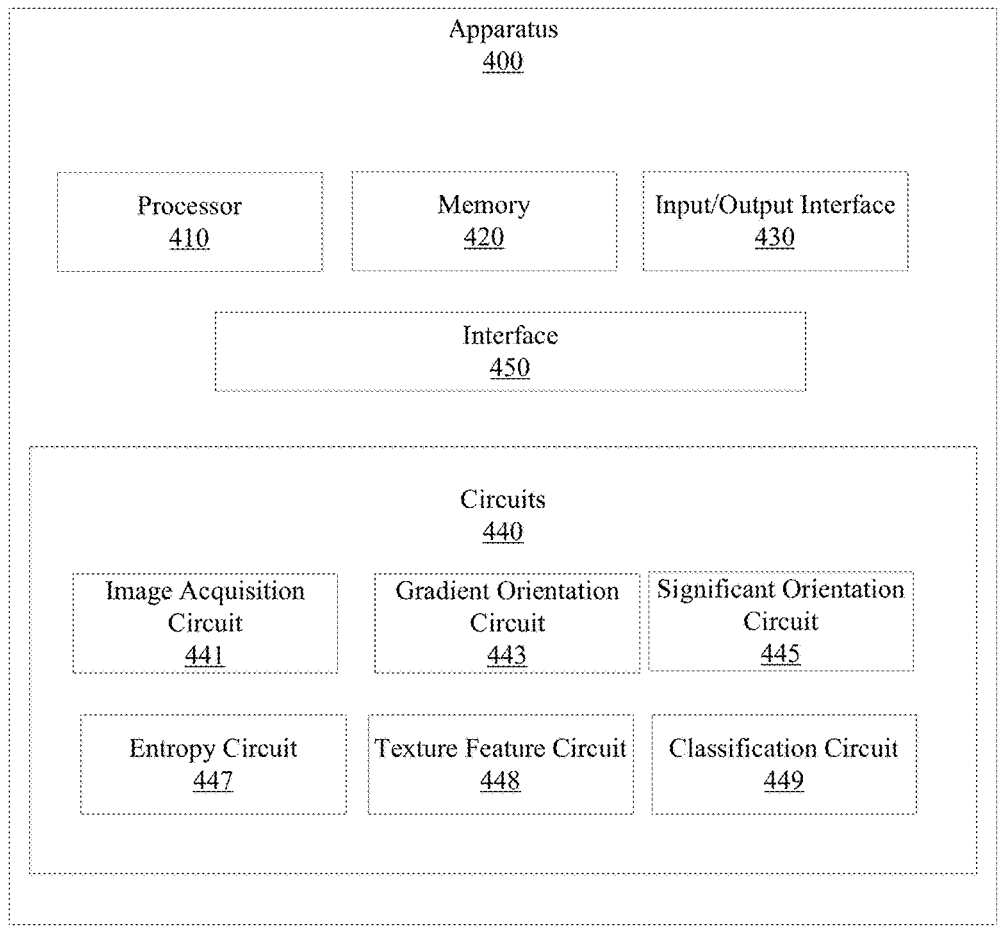
FIG. 4 illustrates an example apparatus that distinguished molecular phenotypes of breast cancer.

FIG. 4 illustrates an example apparatus 400 that distinguishes disease phenotypes or mutational status represented in a ROI obtained from a DCE-MRI of a patient. Apparatus 400 includes a processor 410, a memory 420, an input/output interface 430, a set of circuits 440, and an interface 450 that connects the processor 410, the memory 420, the input/output interface 430, and the set of circuits 440. The set of circuits 440 includes an image acquisition circuit 441, a gradient orientation circuit 443, a significant orientation circuit 445, an entropy circuit 447, a texture feature circuit 448, and a classification circuit 449.

Image acquisition circuit 441 acquires an image of a region of tissue. The region of tissue may be a section of tissue demonstrating cancerous pathology in a patient. In one embodiment, the image is a DCE-MRI image. The DCE-MRI image has a plurality of pixels. A pixel in the DCE-MRI region has an intensity. In one embodiment, the volume illustrated in the DCE-MRI image may be associated with DCE-MRI image of a patient demonstrating breast cancer pathology. In other embodiments, the volume illustrated in the image may be associated with other imaging systems, or be of other regions demonstrating other types of cancer pathology. Thus, accessing the image may include interacting with an MRI system, a computerized tomography (CT) system, or a positron emission tomography (PET) system. Other imaging systems may be used to generate and access the image accessed by image acquisition circuit 441.

Gradient orientation circuit 443 computes a gradient orientation for a pixel in the DCE-MRI image. In one embodiment, gradient orientation circuit 443 computes the gradient orientation as a function of a first-axis intensity gradient for the pixel and a second-axis intensity gradient for the pixel. In another embodiment, gradient orientation circuit 443 may compute the gradient orientation as a function of more than two axes.

Significant orientation circuit 445 computes the most significant orientation for the pixel based on the gradient orientation. In one embodiment, significant orientation circuit 445 uses principal component analysis (PCA) to compute the most significant orientation for the pixel. In another embodiment, the most significant orientation for the pixel may be computed using techniques other than PCA. Significant orientation circuit 445 constructs a localized gradient orientation matrix. Elements of the localized gradient orientation matrix include a first-axis gradient vector for a second pixel. The second pixel may be located within a threshold distance of the first pixel. Elements of the localized gradient orientation matrix also include a second-axis gradient vector for the second pixel. In another embodiment, the localized gradient orientation matrix may include gradient vectors for more than two axes.

Entropy circuit 447 constructs a feature vector. Entropy circuit 447 obtains the values of the feature vector by computing a discretizing entropy distribution for the image. The discretized entropy distribution is based on the most significant orientation of the pixel. The discretized entropy distribution may be obtained from a histogram of the entropy where the histogram is divided into bins. The histogram bin size may be optimized based on a training set using grid search optimization.

Texture circuit 448 extracts a set of texture features from the ROI. The set of texture features includes a set of Laws features. The set of Laws features include energy measures that detect textural patterns that characterize HER2-E or non-HER2-E tissue. The set of Laws features may capture combinations of speckling, rippling, waves, spots, or edge patterns. In one embodiment, the set of Laws features includes at least 25 Laws features. The at least 25 Laws features captures at least one of a speckling pattern, a rippling pattern, a wave pattern, a spottiness pattern, or an edge Classification circuit 449 classifies the phenotype or the mutational status of the cancerous pathology exhibited by the image. In one embodiment, classification circuit 449 classifies the region of tissue as HER2-E or non-HER2-E. In another embodiment, classification circuit 449 classifies the region of tissue as $TP53^{MUT}$ or $TP53^{WT}$. Classification circuit 449 bases the classification, at least in part, on the feature vector and the set of texture features.

In another embodiment, classification circuit 449 may control a computer aided diagnosis (CADx) system to classify the image based, at least in part, on the feature vector and the set of texture features. For example, classification circuit 449 may control a computer aided breast cancer diagnostic system to distinguish the image based, at least in part, on the feature vector and the set of texture features. In other embodiments, other types of CADx systems may be controlled, including CADx systems for distinguishing phenotypes among prostate cancer, colon cancer, lung cancer, bone metastases, and other diseases where disease phenotype or mutational status may be distinguished based on entropy captured in the feature vector and texture features.

In one embodiment of apparatus 400, the set of circuits 440 also includes a display circuit. The display circuit generates a heatmap of the image. The heatmap represents entropy values obtained from localized pixel orientations. Higher entropy values are displayed as a first color and lower entropy values are displayed as a second color. For example, higher entropy values may be displayed as red and lower entropy values may be displayed as blue. The heatmap may display increased expression of HER2-E cancer margins compared to non-HER2-E tissue. The heatmap may display increased expression by HER2-E at both cancer margins and cancer focus, due to speckle and ripple features, compared to non-HER2-E tissue. The heatmap may also display expression of information of measure of correlation within $TP53^{MUT}$ or $TP53^{WT}$ mutant breast cancer studies. The display circuit may control the CADx system to display the classification or the heatmap on a computer monitor, a smartphone display, a tablet display, or other displays. Displaying the classification or the heatmap may also include printing the classification or the heatmap. The display circuit may also control the CADx to display an image of the ROI. The image of the ROI may include a heatmap of the entropy distribution across the ROI. The display circuit may also display a histogram of the entropy of localized gradient orientations.

Figure 5:
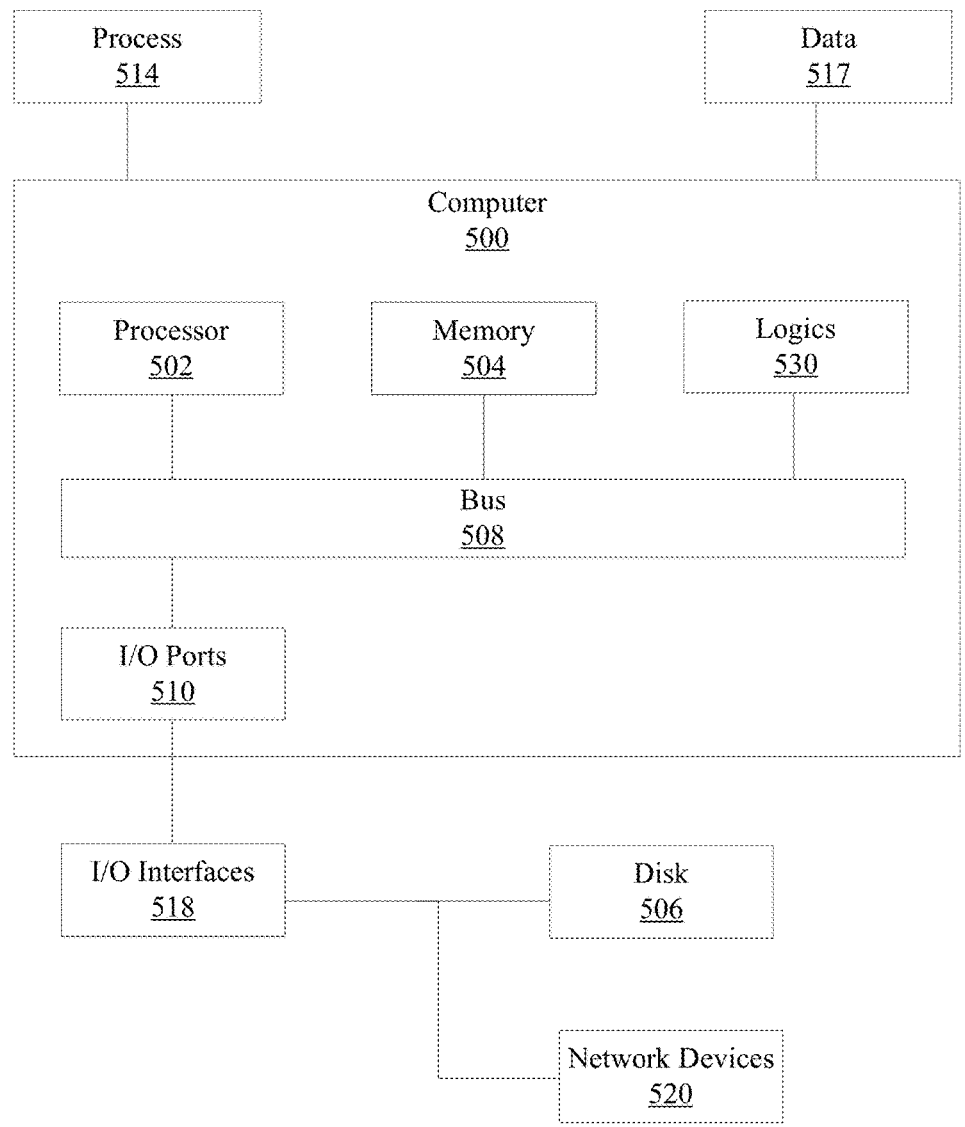
FIG. 5 illustrates an example computer in which example methods and apparatus described herein operate.

FIG. 5 illustrates an example computer 500 in which example methods illustrated herein can operate and in which example logics may be implemented. In different examples, computer 500 may be part of an MRI system, may be operably connectable to an MRI system, or may be part of a CADx system.

Computer 500 includes a processor 502, a memory 504, and input/output ports 510 operably connected by a bus 508. In one example, computer 500 may include a set of logics 530 that perform a method of distinguishing disease phenotypes in a cancer patient using co-occurrence of local anisotropic gradient orientations. Thus, the set of logics 530, whether implemented in computer 500 as hardware, firmware, software, and/or a combination thereof may provide means (e.g., hardware, firmware, circuits) for distinguishing disease phenotypes in a cancer patient using co-occurrence of local anisotropic gradient orientations and Laws features. In different examples, the set of logics 530 may be permanently and/or removably attached to computer 500.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500.

Bus 508 can be a single internal bus interconnect architecture or other bus or mesh architectures. While a single bus is illustrated, it is to be appreciated that computer 500 may communicate with various devices, logics, and peripherals using other buses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), or other networks.

Figure 9:
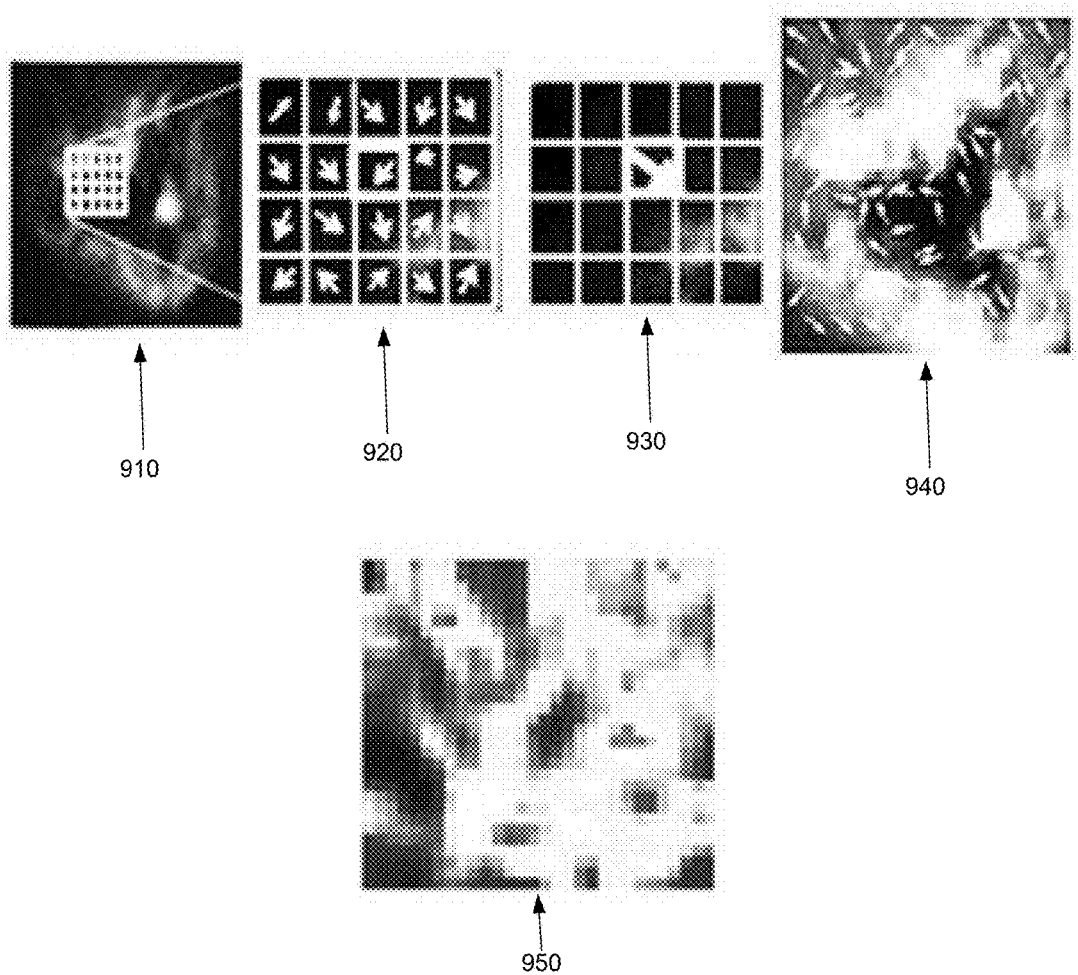
FIG. 9 illustrates steps involved in the extraction of CoLIAGe features from an MRI image.

FIG. 9 is a graphical representation of steps involving the extraction of CoLIAGe features from an ROI in a volume illustrated in a DCE-MRI image in an embodiment of example methods and apparatus. The ROI has a set of pixels, and a pixel in the set of pixels has an intensity. Element 910 illustrates a 5 pixel by 4 pixel neighborhood superimposed on a gray-scale image of an ROI of a region of cancerous tissue. Element 920 illustrates a close-up view of the 5 pixel by 4 pixel neighborhood with pixel-wise gradient orientations represented by directional arrows in each of the cells of the 5 pixel by 4 pixel neighborhood. In one embodiment, the pixel-wise gradient orientations represented in element 920 are calculated at steps 120, 124, and 128 of method 100. Element 930 illustrates the same 5 pixel by 4 pixel neighborhood, but with the dominant gradient orientation for the pixel upon which the neighborhood is centered illustrated. In one embodiment, the dominant gradient orientation illustrated in element 930 corresponds with the dominant gradient orientation calculated at step 140 of method 100. Element 940 illustrates the dominant orientations of the pixels in the ROI superimposed over the gray-scale image of the ROI represented in element 910. FIG. 9 also includes an entropic heatmap 950. In one embodiment, entropic heatmap 950 displays the entropy by the dominant gradient orientations quantified as color ranges. In one embodiment, areas of higher entropy are represented by a first color, and areas of lower entropy are represented by a second, different color.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed by a computer controls the computer to perform a method for distinguishing breast cancer phenotypes using co-occurrence of local anisotropic gradient orientations (Co-LIAGe) and Laws energy features, the method comprising:
   accessing a region of interest (ROI) in a volume illustrated in a magnetic resonance image (MRI), the ROI having a set of pixels, where a pixel in the set of pixels has an intensity;
   obtaining an x-axis gradient for a first pixel in the set of pixels based, at least in part, on the intensity of the pixel;
   obtaining a y-axis gradient for the first pixel based, at least in part, on the intensity of the pixel;
   computing an x-axis gradient vector for a second pixel in an N pixel by N pixel neighborhood centered around the first pixel, N being a number;
   computing a y-axis gradient vector for the second pixel in the N pixel by N pixel neighborhood;

constructing a localized gradient vector matrix based, at least in part, on the x-axis gradient vector for the second pixel, and the y-axis gradient vector for the second pixel;
computing a dominant orientation for the first pixel based, at least in part, on the localized gradient vector matrix;
constructing a co-occurrence matrix from the dominant orientation;
computing an entropy for the first pixel based, at least in part, on the co-occurrence matrix;
obtaining a distribution of the entropy;
constructing a feature vector based, at least in part, on the distribution of the entropy;
extracting a set of texture features from the ROI; and
controlling a phenotype classifier to classify the ROI based, at least in part, on the feature vector and the set of texture features.

2. The non-transitory computer-readable storage device of claim 1, where the volume illustrated in the MRI is associated with a dynamic contrast enhanced (DCE) MRI image of a patient demonstrating breast cancer pathology.

3. The non-transitory computer-readable storage device of claim 2, where the set of texture features includes a Laws feature, where the Laws feature is based on a two dimensional (2D) filter targeting speckling, rippling, waves, spottiness, or edges represented in the volume illustrated in the MRI.

4. The non-transitory computer-readable storage device of claim 3, where controlling the phenotype classifier to classify the ROI includes distinguishing human epidermal growth factor receptor enriched (HER2-E) breast cancer subtype from human epidermal growth factor receptor positive (HER2+) breast cancer in the ROI.

5. The non-transitory computer-readable storage device of claim 4, where controlling the phenotype classifier to classify the ROI includes distinguishing HER2-E from human epidermal growth factor receptor luminal (HER2-L) breast cancer subtype or human epidermal growth factor receptor basal (HER2-B) breast cancer subtype, or distinguishing HER2-B from HER2-E or HER2-L.

6. The non-transitory computer-readable storage device of claim 5, where the phenotype classifier distinguishes HER2-E from HER2-L or HER2-B based, at least in part, on the feature vector, the entropy, or the distribution of the entropy.

7. The non-transitory computer-readable storage device of claim 5, where the phenotype classifier distinguishes HER2-B from HER2-E or HER2-L based, at least in part, on a kurtosis value or a skewness value of pixel-wise entropy or the Laws feature.

8. The non-transitory computer-readable storage device of claim 3, where controlling the phenotype classifier to classify the ROI includes predicting a TP53 mutational status of breast cancer tissue represented in the ROI.

9. The non-transitory computer-readable storage device of claim 8, where predicting a TP53 mutational status comprises:
computing a skewness measure of correlation and a kurtosis measure of correlation based on the co-occurrence matrix; and
classifying the ROI as $TP53^{MUT}$ or $TP53^{WT}$ based, at least in part, on the feature vector, the skewness measure, and the kurtosis measure.

10. The non-transitory computer-readable storage device of claim 9, where the skewness measure includes an inertia feature, a sum average feature, or a difference feature variance, and where the kurtosis measure includes an energy feature, an entropy feature, or a correlation feature.

11. A non-transitory computer-readable storage device storing computer-executable instructions that when executed by a computer controls the computer to perform a method for distinguishing disease phenotypes, the method comprising:
accessing a region of interest (ROI) in a volume illustrated in a radiologic image, where the ROI has a set of pixels, and where a pixel in the set of pixels has an intensity;
computing a local dominant gradient orientation for a first pixel in the set of pixels;
constructing a co-occurrence matrix for the set of pixels, based, at least in part, on the local dominant orientation;
computing an entropy measure for the set of pixels based, at least in part, on the co-occurrence matrix;
constructing a feature vector based on a distribution of the entropy measure;
extracting a set of texture features from the ROI; and
controlling a disease phenotype classification system to classify the ROI as human epidermal growth factor receptor enriched (HER2-E) breast cancer subtype or human epidermal growth factor receptor positive (HER2+) breast cancer based, at least in part, on the feature vector and the set of texture features.

12. The non-transitory computer readable storage device of claim 11, where computing the local dominant gradient orientation for the first pixel includes:
obtaining a set of gradients for the first pixel along a plurality of axes;
computing a gradient orientation for the pixel based, at least in part, on the set of gradients;
computing a set of gradient vectors for a plurality of pixels in a neighborhood, where the neighborhood is centered on the first pixel;
constructing a localized gradient vector matrix from the set of gradient vectors; and
computing the local dominant gradient orientation for the first pixel using principal component analysis (PCA) based, at least in part, on the localized gradient vector matrix.

13. The non-transitory computer readable storage device of claim 12, where constructing the co-occurrence matrix includes:
discretizing the local dominant gradient orientation for the first pixel; and
populating the co-occurrence matrix with local dominant gradient orientation pairs that co-exist between pixels in the neighborhood.

14. The non-transitory computer readable storage device of claim 13, where computing the entropy measure includes:
aggregating the entropy measure for a subset of the set of pixels, where the entropy measure is based, at least in part, on the co-occurrence matrix; and
constructing a histogram of the entropy measure for set of pixels, where the histogram is divided into bins, where a bin has a threshold size.

15. The non-transitory computer readable storage device of claim 14, where constructing the feature vector includes extracting entropy measure values from a distribution of the histogram.

16. The non-transitory computer readable storage device of claim 15, where controlling the disease phenotype classification system includes constructing a heatmap based on the feature vector and the set of texture features, where hot areas of the heatmap represent high entropy values, and where cool areas of the heatmap represent low entropy values.

17. An apparatus for distinguishing disease phenotypes, comprising:
a processor;
a memory;
an input/output interface;
a set of circuits; and
an interface to connect the processor, the memory, the input/output interface and the set of circuits, where the set of circuits includes:
an image acquisition circuit that acquires a radiologic image of a region of tissue demonstrating cancerous pathology, where the radiologic image has a plurality of pixels, where a pixel has an intensity;
a gradient orientation circuit that computes a gradient orientation for a pixel in the radiologic image based, at least in part, on an first-axis intensity gradient for the pixel and a second-axis intensity gradient for the pixel;
a significant orientation circuit that computes the most significant orientation for the pixel based on the gradient orientation;
an entropy circuit that constructs a feature vector, where the values of the feature vector are obtained by computing a discretized entropy distribution for the image based on the most significant orientation of the pixel;
a texture feature circuit that extracts a set of texture features from the radiologic image; and
a classification circuit that classifies the phenotype or mutational status of the cancerous pathology exhibited by the image based, at least in part, on the feature vector and the set of texture features.

18. The apparatus of claim 17, where the significant orientation circuit uses principal component analysis (PCA) to compute the most significant orientation for the pixel by constructing a localized gradient vector matrix, where elements of the localized gradient vector matrix include a first-axis gradient vector for a second pixel located within a threshold distance of the first pixel, and a second-axis gradient vector for the second pixel.

19. The apparatus of claim 17, where the texture feature circuit extracts at least 25 Laws features from the radiologic image, where the at least 25 Laws features captures at least one of a speckling pattern, a rippling pattern, a wave pattern, a spottiness pattern, or an edge.

20. The apparatus of claim 17, comprising a display circuit that generates a heatmap of the image, where the heatmap represents entropy values obtained from localized pixel orientations or the set of texture features, where the heatmap displays higher entropy values as a first color and lower entropy values as a second, different color.

* * * * *